United States Patent
Huntington

(10) Patent No.: US 10,960,259 B2
(45) Date of Patent: Mar. 30, 2021

(54) HIP-STRETCHING DEVICE

(71) Applicant: Timothy J. Huntington, Murrieta, CA (US)

(72) Inventor: Timothy J. Huntington, Murrieta, CA (US)

(*) Notice: Subject to any disclaimer, the term of this patent is extended or adjusted under 35 U.S.C. 154(b) by 126 days.

(21) Appl. No.: 16/004,083

(22) Filed: Jun. 8, 2018

(65) Prior Publication Data
US 2019/0374809 A1   Dec. 12, 2019

(51) Int. Cl.
*A63B 21/00* (2006.01)
*A63B 23/04* (2006.01)
*A63B 21/002* (2006.01)
*A61F 7/02* (2006.01)
*A63B 23/00* (2006.01)

(52) U.S. Cl.
CPC ............ *A63B 21/4037* (2015.10); *A61F 7/02* (2013.01); *A63B 21/002* (2013.01); *A63B 21/00185* (2013.01); *A63B 21/151* (2013.01); *A63B 21/4005* (2015.10); *A63B 21/4011* (2015.10); *A63B 21/4025* (2015.10); *A63B 23/0482* (2013.01); *A63B 2023/006* (2013.01); *A63B 2225/62* (2013.01)

(58) Field of Classification Search
CPC ............ A63B 21/4037; A63B 23/0482; A63B 21/002; A63B 21/4005; A63B 21/4011; A63B 21/151; A63B 21/4025; A63B 21/00185; A63B 2225/62; A63B 2023/006; A63B 2225/09; A63B 2209/00; A63B 2209/10; A63B 2208/0252; A63B 1/00; A61F 7/02
See application file for complete search history.

(56) References Cited

U.S. PATENT DOCUMENTS

| | | | | |
|---|---|---|---|---|
| 4,943,053 A | * | 7/1990 | Smith | A63B 21/0085 482/113 |
| 5,110,083 A | | 5/1992 | Page | |
| 5,122,106 A | * | 6/1992 | Atwood | A61H 1/0244 482/131 |
| 5,338,276 A | * | 8/1994 | Jull | A63B 21/0085 482/111 |
| 5,713,841 A | * | 2/1998 | Graham | A61H 1/0218 602/32 |
| 5,906,586 A | * | 5/1999 | Graham | A61F 5/04 128/845 |
| 6,110,083 A | * | 8/2000 | Riser | A63B 21/154 482/142 |

(Continued)

*Primary Examiner* — Garrett K Atkinson
(74) *Attorney, Agent, or Firm* — Stinson LLP

(57) ABSTRACT

A hip-stretching device includes a mat having an upper surface. The mat is configured for placement on a support surface to support a back of a subject lying in a supine position on the upper surface of the mat. The hip-stretching device includes first and second pockets associated with the mat. The first and second pockets each have an opening configured to removably receive an inflatable bladder for selectively placing the inflatable bladder in one of the first and second pockets. The first and second pockets each position an inflatable bladder received therein under a hip area of the subject when the subject is lying in the supine position on the upper surface of the mat. Inflation of the inflatable bladder imparts a force to the hip area of the subject to elevate the hip area to provide a hip flexor stretch to the subject.

20 Claims, 6 Drawing Sheets

(56) References Cited

U.S. PATENT DOCUMENTS

| | | | | |
|---|---|---|---|---|
| 6,458,147 B1* | 10/2002 | Cruise | ............... | A61P 7/04 |
| | | | | 606/214 |
| 9,114,270 B2* | 8/2015 | Aldridge | ............... | A61H 1/0237 |
| 9,420,895 B2* | 8/2016 | Lafleche | ............... | A47C 27/081 |
| 2006/0160673 A1* | 7/2006 | Tennant | ............... | A61H 1/0244 |
| | | | | 482/91 |
| 2010/0152003 A1* | 6/2010 | Haas | ............... | A63B 69/0057 |
| | | | | 482/95 |
| 2011/0302720 A1* | 12/2011 | Yakam | ............... | A61G 7/05776 |
| | | | | 5/710 |
| 2012/0058861 A1* | 3/2012 | Satut | ............... | A63B 6/00 |
| | | | | 482/8 |
| 2012/0283080 A1* | 11/2012 | Mayr | ............... | A63B 24/0006 |
| | | | | 482/142 |
| 2014/0194266 A1* | 7/2014 | Raiten | ............... | A63B 21/4011 |
| | | | | 482/142 |
| 2015/0238123 A1* | 8/2015 | Yakam | ............... | A47C 27/082 |
| | | | | 340/573.1 |

\* cited by examiner

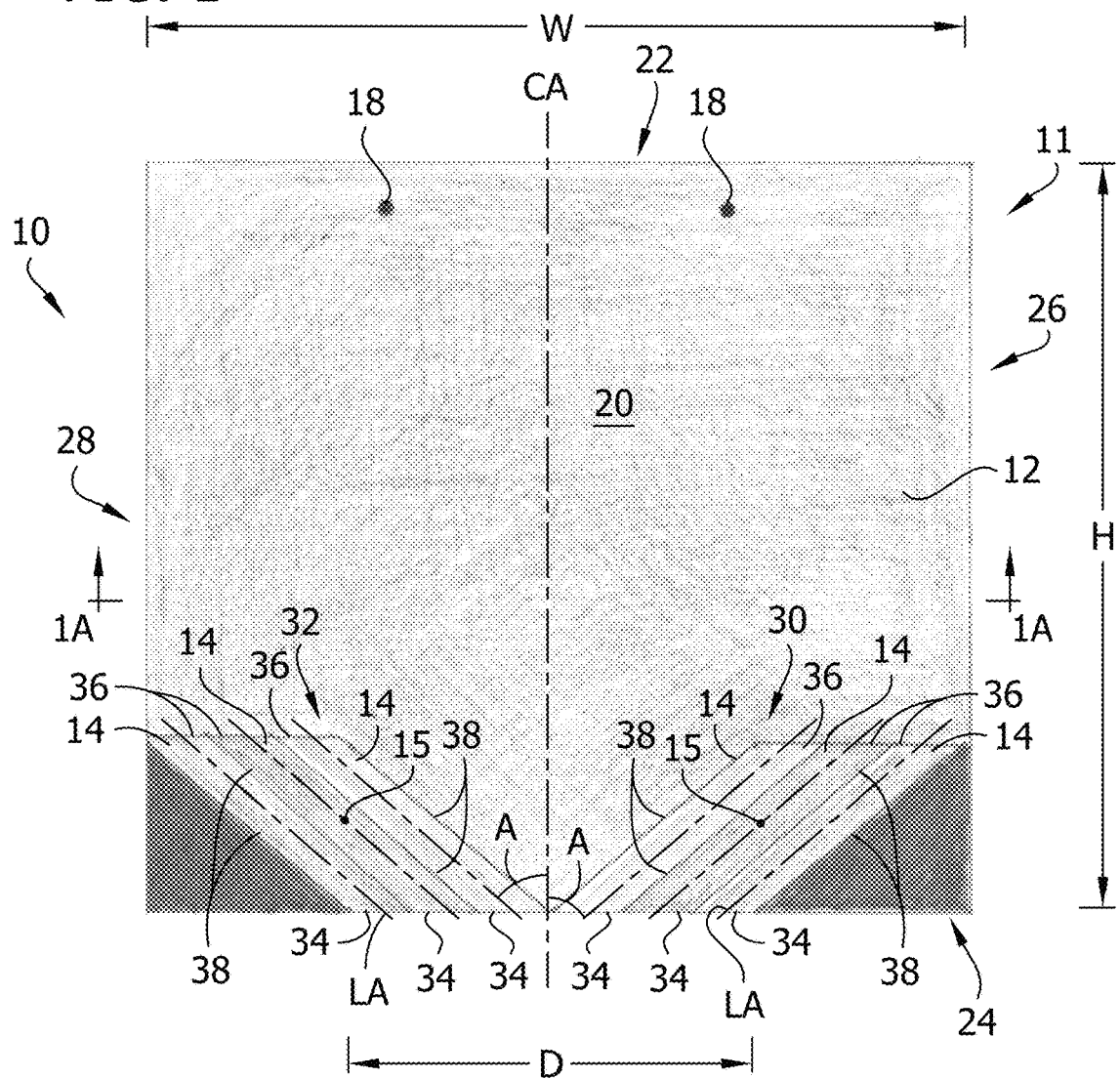
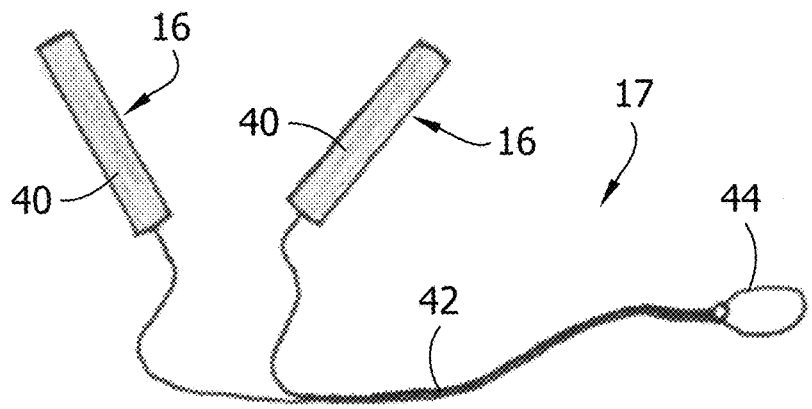
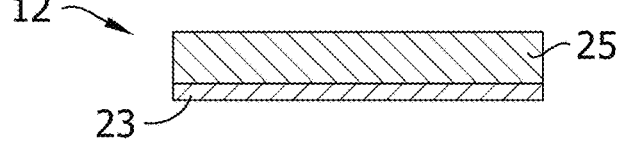

US 10,960,259 B2

HIP-STRETCHING DEVICE

FIELD OF THE INVENTION

The present disclosure generally relates to stretching a person's hip flexors, and more specifically, to a stretching device and method used to stretch a person's hip flexors.

BACKGROUND

Stretching of the hip is a common and important activity. Athletes stretch to prepare their bodies for a sporting event. Likewise, patients stretch to aid in the recovery and rehabilitation process after experiencing a traumatic event, and in the interest of preventing subsequent injury. The psoas major, psoas minor and iliacus muscles (collectively "the hip flexors") of each hip joint are commonly stretched by a person lying in a supine position (lying face up). In the supine position, the person grasps a knee of one leg and brings it toward their chest. The person extends their other leg and holds this position for a period of time to stretch the hip flexor on the extended leg. After the hip flexor is stretched for the desired period of time, the person switches to the other leg and repeats the process to stretch the other hip flexor.

SUMMARY

In one aspect, a hip-stretching device comprises a mat having an upper surface and configured for placement on a support surface to support a back of a subject lying in a supine position on the upper surface of the mat. The hip-stretching device further comprises first and second pockets associated with the mat. The first and second pockets have an opening configured to removably receive an inflatable bladder for selectively placing the inflatable bladder in one of the first and second pockets. The first and second pockets each position an inflatable bladder received therein under a hip area of the subject when the subject is lying in the supine position on the upper surface of the mat such that inflation of the inflatable bladder imparts a force to the hip area of the subject to elevate the hip area providing a hip flexor stretch to the subject.

In another aspect, a method of stretching a hip flexor of a person comprises providing a hip-stretching device which includes a mat with at least two pockets and an inflatable bladder configured to be removably inserted into one of the at least two pockets, inserting the inflatable bladder into one of the at least two pockets, laying the mat on a support surface and positioning the mat underneath the person such that the inflatable bladder inserted into one of the at least two pockets is disposed beneath a hip flexor of the person, and inflating the inflatable bladder to stretch the hip flexor.

BRIEF DESCRIPTION OF THE DRAWINGS

FIG. 1 is an illustration of a hip-stretching device of the present disclosure with straps removed and an inflatable bladder assembly shown separated from a pad assembly;

FIG. 1A is a section of the pad assembly taken through line 1A-1A in FIG. 1;

Corresponding reference characters indicate corresponding parts throughout the drawings.

DETAILED DESCRIPTION

Figure 3:
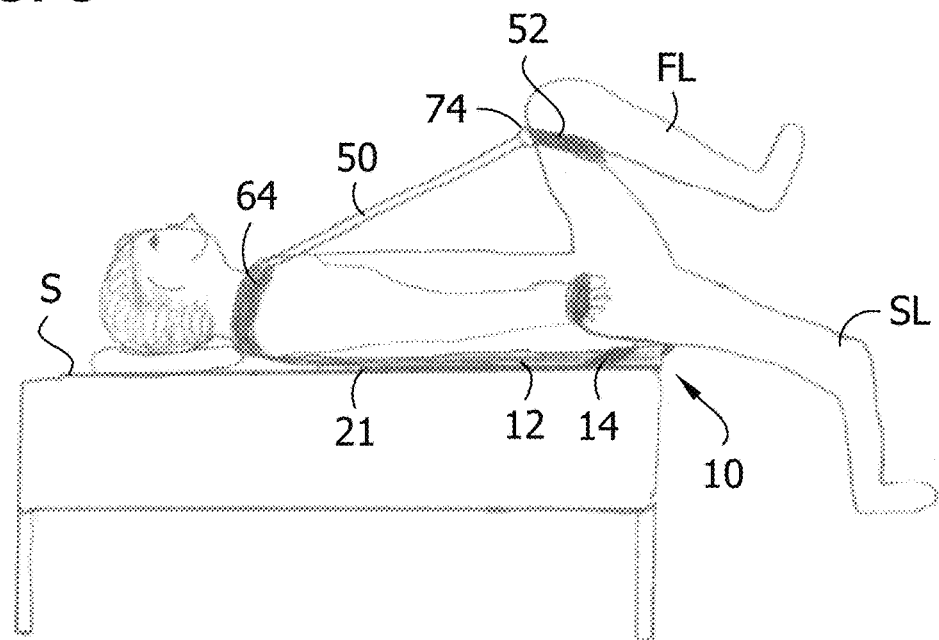
FIG. 3 is an illustration of the hip-stretching device in use during a high-intensity stretch.

Referring to FIGS. 1 and 3, a hip-stretching device of the present disclosure is generally indicated at 10. The hip-stretching device 10 comprising a pad or mat assembly 11 including a mat 12 and a plurality of pockets 14 associated with the mat that hold one or more inflatable bladders 16 of a bladder assembly 17. As will be discussed in more detail below, in use, a person lies down in a supine position (face up) on the mat 12 and positions their hips over the pockets 14 (FIG. 8) with the inflatable bladders 16 received in the pockets. Once in position, the person uses the device 10 to position their legs to stretch their hip flexors. As will be explained in greater detail below, the person can inflate the inflatable bladders 16 in the pockets 14 under their hips to elevate the hips and, thereby, further stretch the hip flexors through the process of a controlled isokinetic release and desensitization of the stretch receptors within the hip flexor muscle group.

Referring to FIGS. 1-2, the pad assembly 11 includes a flat pad or mat 12 with opposite upper and lower surfaces 20 and 21, opposite top and bottom edge margins 22 and 24, and opposite first and second side edge margins 26 and 28. A central axis CA extends between the top and bottom edge margins 22, 24. The mat 12 includes two connector components 18 secured to the mat on opposite sides of the central axis CA. As described in more detail below, the connection portion of the connector component 18 is located on or near the lower surface 21 of the mat 12. In the preferred embodiment, the mat 12 has a plastic base 23 with a foam or rubber sheet 25 joined on top. In one embodiment, the plastic base is about 2 to about 4 mm (about 0.08 to about 0.16 inches) thick. The foam or rubber sheet 25 is deformable to provide a measure of comfort when the person is in the supine position on the upper surface 20 of the mat 12 (e.g. the person lays on the upper surface of the foam or rubber sheet). The plastic base 23 and foam or rubber sheet 25 can be adhered together using glue or any other suitable method. The mat 12 has a height H extending between the top and bottom edge margins 22,24 and a width W extending between the opposite first and second side edge margins 26, 28. In the preferred embodiment, the mat has a height of about 18 inches (about 46 cm) and a width of about 20 inches (about 51 cm); however, other sizes are within the scope of the present disclosure. As used throughout the present disclosure with respect to the hip-stretching device, the terms defining relative locations and positions of structures and components of the device, including but not limited to the terms "top," "bottom," "side," and "front," are meant to provide a point of reference for such components and structures as shown in the drawings, with the understanding that the respective relative locations of such components and structures will depend on the orientation of the device in use.

Referring to FIG. 1, the pad assembly 11 includes a plurality of pockets 14 associated with the mat 12 and configured to receive the one or more inflatable bladders 16. In the illustrated embodiment, the pockets 14 are formed in the mat 12, adjacent the bottom edge margin 24 of the pad assembly 11. The pockets 14 are divided into two sets: a first set of pockets 30 located to one side of the central axis CA and a second set of pockets 32 located to the opposite side of the central axis. Each set of pockets 30, 32 is made up of one or more individual pockets 14. In the illustrated embodiment, each set of pockets 30, 32 is comprised of three individual pockets 14, however, different amounts of individual pockets in each set is within the scope of the present disclosure. In the illustrated embodiment, the individual pockets 14 of each set 30, 32 are immediately adjacent or touching one another such that the immediately adjacent pockets share an edge (e.g. sides 38), however, it is understood that the individual pockets 14 can be spaced part (e.g. do not share an edge).

Figure 8:
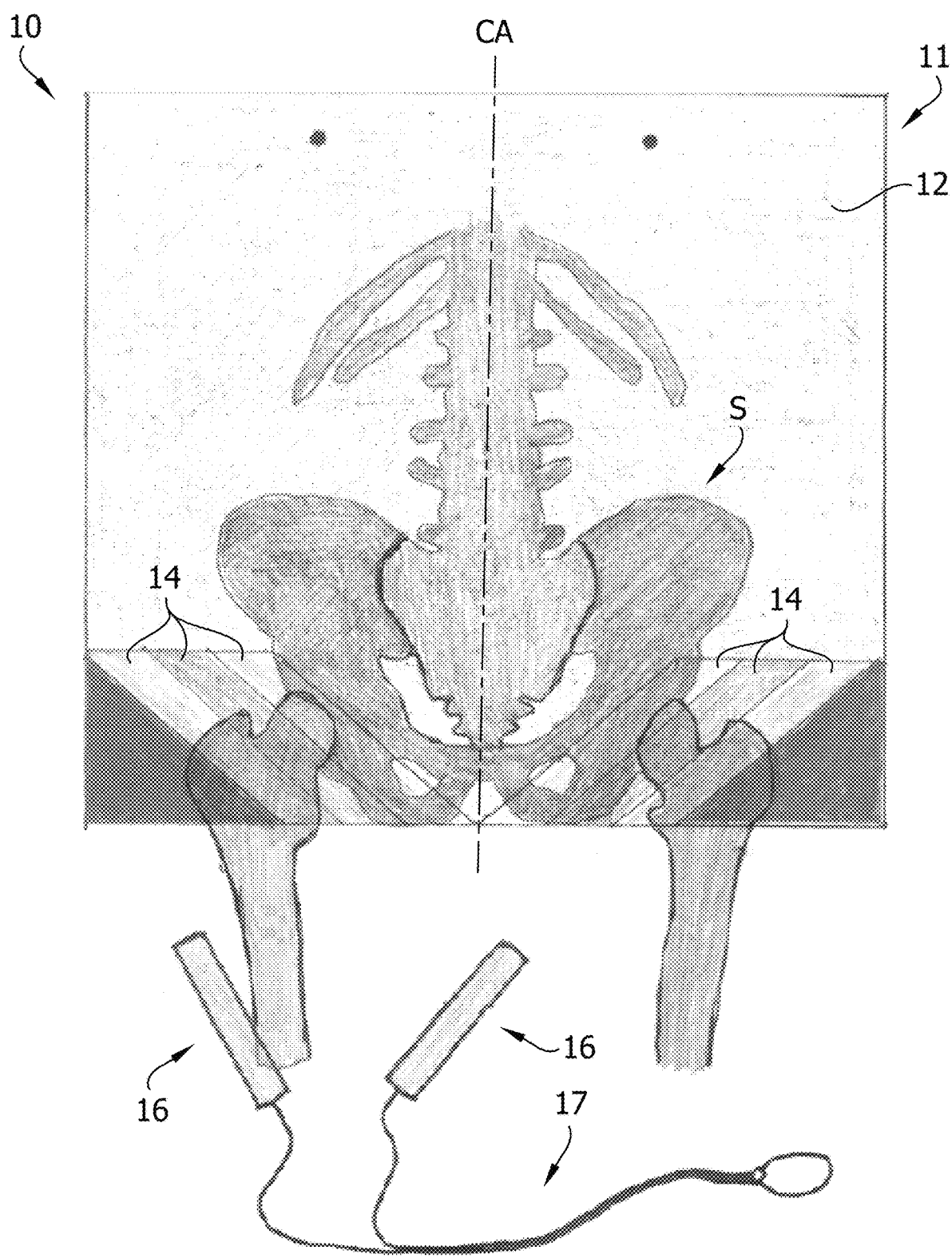
FIG. 8 is an illustration of a portion of a person's skeletal system oriented on the pad assembly of FIG. 1.

The first set of pockets 30 is positioned to underlie one hip of the person and the second set of pockets 32 is positioned to underlie the other hip when the person is in the supine position on the mat 12 (FIG. 8). The first and second sets of pockets 30, 32 are located proximate to one another. In the illustrated embodiment, the pockets 14 of the first and second sets 30, 32 closest to the center of the mat 12 engage each other along the bottom edge margin 24 at the central axis CA. In the preferred embodiment, first and second sets of pockets 30, 32 are arranged such that a centerpoint 15 of the center pockets 14 of each set are spaced apart by a distance D that is between about 9 and about 12 inches (about 23 to about 31 cm) and more preferably a distance of about 10.2 inches (26 cm). This distance corresponds to the average pelvic width of humans. However, it is understood the first and second set of pockets 30, 32 can have other arrangements that are within the scope of the present disclosure. It is further envisioned that the pockets 14 can be formed separately from the mat 12 and suitably attached and/or positioned at a bottom edge margin of the mat.

The individual pockets 14 in the first and second sets 30, 32 are set at different angles relative to the central axis CA but are otherwise identical in structure and function, and therefore, reference will be made to one pocket for ease of description with the understanding that the following description applies equally to each of the individual pockets 14. The pocket 14 defines an open interior (not shown) that is sized and shaped to receive one of the inflatable bladders 16. The pocket 14 has an opening 34 located proximate to the bottom edge margin 24, a closed end 36 opposite the opening, and opposite sides 38 extending between the opening and the closed end. The closed end 36 of the pocket 14 is located inside a perimeter of the mat 12 defined by the top, bottom and opposite side edge margins 22, 24, 26 and 28. The pocket 14 has a width between opposite sides 38 generally corresponding to a width of the inflatable bladder 16 and a length between the opening 34 and the closed end 36 generally corresponding to a length of the inflatable bladder. In the preferred embodiment, the pocket 14 has a width of about 2 inches (about 5 cm) and a length of about 5 inches (about 13 cm). However, the pocket 14 can have other shapes and sizes than described herein to correspond to the shape and size of the inflatable bladders 16. A longitudinal axis LA extends between the opening 34 and closed end 36 of the pocket 14. The longitudinal axis LA extends at an angle A relative to the central axis CA. In the preferred embodiment, the pocket 14 is oriented such that the angle A between the longitudinal axis LA of the pocket and the central axis CA is between about 30° and about 50° and more preferably at about 39°. This angle generally corresponds to the typical joint angle of a person's pelvo-femoral hip joint, which underlies the location of the hip flexors (FIG. 8). In this manner, the pocket 14 is angled toward either side edge margin 26, 28 of the mat 12 as the pocket extends from the opening 34 to the closed end 36. In the preferred embodiment, the pocket 14 is elastic or stretchable to accommodate the variations in size as the inflatable bladder is inflated and deflated, as described in more detail below.

The pockets 14 in the first and second sets 30, 32 are arranged to correspond to the angle of the hip joint each set of pockets will underlie. Thus, the pockets 14 comprising the first set of pockets 30 have longitudinal axes LA angled toward the first side edge margin 26 and the pockets comprising the second set of pockets 32 have longitudinal axes angled toward the second side edge margin 28. The longitudinal axes LA of the pockets 14 in the first set 30 are generally parallel to each other and the longitudinal axes of the pockets in the second set 32 are generally parallel to each other. However, the longitudinal axis LA of the pockets 14 in the first set 30 are in a non-parallel arrangement with the pockets 14 in the second set 32.

Referring to FIG. 1, the bladder assembly 17 includes one or more inflatable bladders 16 attached to a pump 44 by a tube 42. Each inflatable bladder 16 is removably received in the open interior of a pocket 14 through the opening 34 such that the inflatable bladder can be moved between and be received in any one of the pockets. In the preferred embodiment, the bladder assembly 17 includes two inflatable bladders 16 such that one inflatable bladder can be received in each set of pockets 30, 32. The inflatable bladder 16 has a flexible body 40 with opposite ends defining an inflatable interior. In the illustrated embodiment, the inflatable bladders 16 are generally cylindrically shaped (when inflated), however, it is understood the inflatable bladders can have other shapes than described herein without departing from the scope of the present disclosure. One end of the inflatable bladder 16 is closed and the other end is connected to a distal end of a fluid conduit or tube 42 such that the tube is in fluid communication with the inflatable interior. A proximal end of the tube 42 is connected to and in fluid communication with a pump 44. Where two or more inflatable bladders 16 are included, each inflatable bladder can be fluidly connected to the pump with separate tubes or a single tube can have multiple branches connected to each inflatable bladder (e.g. the tube branches to have multiple distal ends, each distal end connected to an inflatable bladder). The pump 44, via the tube 42, is in fluid communication with the inflatable interior of the inflatable bladders 16. The pump 44 is configured to direct air into the inflatable interior, thereby inflating the inflatable bladder 16. In the preferred embodiment, the pump 44 is manually operated by the user's hand; however, other pumps are within the scope of the present disclosure, such as powered pumps. A valve (not shown) may be connected to the pump 44 and/or the tube 42 and be in fluid communication with the inflatable bladder 16. The valve allows air to escape from the inflatable bladder 16 to deflate the inflatable bladder. In the preferred embodiment, the valve is a small, needle sized air release hole in the pump 44 that the user selectively places their hand or finger over to form a seal and selectively deflate the inflatable bladder.

In this manner, by selectively covering the air release hole, the user can control the rate the inflatable bladder 16 as it deflates. In one embodiment, to achieve the therapeutic release and stretch of the hip flexors, the inflatable bladder will automatically deflate in about three minutes if the user chooses to deflate without manual intervention. However, other valves and valve configurations are within the scope of the present disclosure.

Figure 2A:
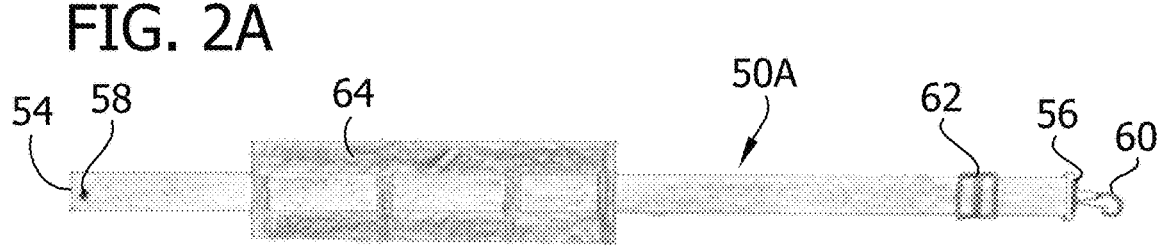
FIG. 2A is an illustration of a shoulder strap of the hip-stretching device.
Figure 2B:
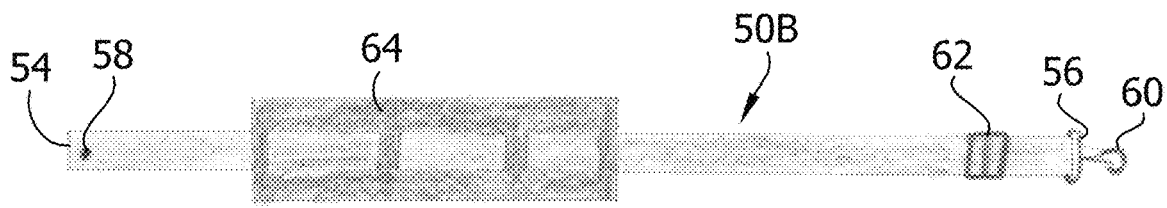
FIG. 2B is an illustration of another shoulder strap of the hip-stretching device.
Figure 2C:
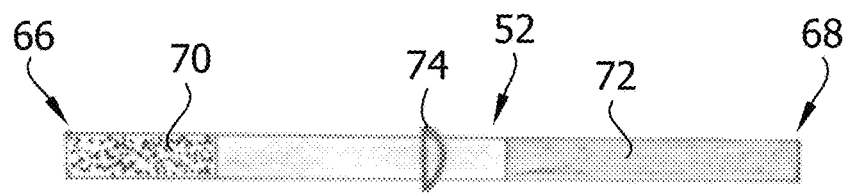
FIG. 2C is an illustration of a knee strap of the hip-stretching device.

Referring to FIGS. 2A-C, the hip-stretching device includes identical first and second shoulder straps 50A, 50B and a knee strap 52. The shoulder straps 50A, 50B and the knee strap 52 hold the person's knee in place to stretch the hip flexors of the opposite limb. In addition, the shoulder straps 50A, 50B and the knee strap 52 hold the person's knee in a supportive flexed position to stabilize the pelvis and lumbar spine to allow for greater comfort in the stretching of the hip flexors. Each shoulder strap 50A, 50B has a proximal end 54 and a distal end 56 with a length therebetween. The proximal end 54 of the shoulder strap 50A, 50B is configured to be attached or secured to the mat 12. A connector component 58, attachable to the connector component 18 on the mat 12, is secured to the proximal end 54 of each shoulder strap 50A, 50B. By attaching the two connector components 18, 58 together, the proximal end 54 of the shoulder strap 50A, 50B can be secured to the mat 12. In the preferred embodiment, the connector components 18, 58 comprise the male and female portions of a button snap; however, other methods of attaching the shoulder straps 50A, 50B to the mat 12 are within the scope of the present disclosure. The distal end 56 of each shoulder strap 50A, 50B is configured to releasably attach to the knee strap 52. A clip 60 is attached to the distal end 56 of the shoulder strap 50A, 50B and can be releasably connected to the knee strap 52 by clipping the clip 60 to a ring 74 of the knee strap. Each shoulder strap 50A, 50B includes a buckle 62 positioned between the proximal and distal ends 54, 56. The buckle 62 is located closer to the distal end 56 and receives an end portion of the strap 50A, 50B that is folded back on itself, creating a loop the clip 60 is attached to. The buckle 62 also allows the length of the shoulder strap 50A, 50B to be adjusted by either moving the buckle along the strap or moving the end portion of the strap through the buckle. A shoulder pad 64 is movably connected to the shoulder strap 50A, 50B. In the illustrated embodiment, the shoulder strap 50A, 50B is inserted through the shoulder pad 64.

The knee strap 52 has a shorter length than the shoulder strap 50A, 50B and is sized to be wrapped around the person's leg just above the knee. The knee strap has a proximal end 66 and a distal end 68. The knee strap includes Velcro so that the knee strap can be secured around the leg of the person and attached to itself. In the illustrated embodiment, the hook section 70 of the Velcro is attached to the proximal end 66 and extends over a portion of the knee strap 52 toward the distal end 68. Likewise, the loop section 72 of the Velcro is attached to the distal end 68 and extends over a portion of the knee strap 52 toward the proximal end 66. It is appreciated that the Velcro sections 70, 72 are located on opposite sides of the knee strap 52 so that the Velcro sections can engage and connect to each other when the strap is wrapped around the leg of the person. A ring 74 is connected to the knee strap 52. The clips 60 of the shoulder straps 50A, 50B engage the ring 74 of the knee strap 52, thereby connecting the shoulder straps to the knee strap. The ring 74 can be freely movable along the knee strap 52 or fixedly attached. The shoulder straps 50A, 50B and knee strap 52 can be made from nylon, polypropylene, polyester or any other suitable material.

Referring to FIGS. 3-5 and 8, the hip-stretching device 10 is shown in use. To set up the hip-stretching device 10, the person inserts one inflatable bladder 16 into one of the three pockets 14 in the first set 30 and inserts the other inflatable bladder 16 into one of the three pockets 14 in the second set 32. The person chooses which pockets 14 in each set 30, 32 to insert the inflatable bladders 16 into based upon their pelvic width—the distance between the two hip joints, and therefore the hip flexors, of the person. For example, a person with an average pelvic width of about 10.2 inches (about 26 cm) would insert the inflatable bladders 16 into the center pockets 14 of the first and second sets 30, 32. The skeletal outline S of a person with an average pelvic width is shown in FIG. 8. In this illustration, the skeletal outline S is opaque to show the two hip joints generally over the center pockets 14 when the person is in the supine position. Moreover, a person with a larger pelvic width may insert the inflatable bladders 16 in the outer-most pockets 14 of the first and second sets 30, 32, or a person with a smaller pelvic width may insert the inflatable bladders in the inner-most pockets of the first and second set. Other configurations are also possible. Accordingly, the different pockets 14 allow the hip-stretching device 10 to be adapted to the specific pelvic width of the person using the device. If the hip-stretching device 10 only includes one inflatable bladder 16, that inflatable bladder is positioned under the hip area of the hip flexor to be stretched. Once the inflatable bladders 16 are positioned in the desired pockets 14, the proximal end 54 of each shoulder strap 50A, 50B is attached to the mat 12 using the connector components 18, 58.

To stretch the hip flexors, the person positions the hip-stretching device 10 on a flat support surface S. The support surface S can be a bed, a floor, or any other flat surface that can support the person lying in a supine position on the mat 12. In the illustrated embodiment, the support surface S is a bed. The person then aligns their body with the hip-stretching device 10 and lies down in the supine position onto the upper surface 20 of the mat 12 such that the person's spine is generally aligned with the central axis CA of the mat 12 (FIG. 8). In the supine position, the persons back is supported by the upper surface 20 of the mat 12 with the shoulders positioned proximate the top edge margin 22 and the lower back positioned proximate the bottom edge margin 24. In particular, the person has positioned their body such that the hips or hip area is aligned with the inflatable bladders 16 received in the pockets 14 of the mat 12.

The user secures the knee strap 52 around the flex leg FL, which is the opposite leg to the stretch leg SL with the desired hip flexor to be stretched. The knee strap 52 can be secured after the person is in the supine position or the person may find it easier to secure the knee strap before lying down. Once the knee strap 52 is secured and the person is in the supine position, the person moves both shoulder strap 50A, 50B over the shoulders and attaches the clip 60 to the ring 74 of the knee strap 52. The person moves the shoulder pads 64 along the strap 50A, 50B so that the pads engage the person's shoulders. Using both shoulder straps 50A, 50B provides greater stability of the knee of the flexed leg FL during the stretch of the hip flexor on the stretch SL. Because the connector components 18 are positioned on the lower surface 21 of the mat 12, a portion of the shoulder straps 50A, 50B extend under the mat 12. When the person is in the supine position, the compression of the shoulder straps 50A, 50B between the support surface S and the mat 12 helps keep the shoulder straps attached to the mat during the hip flexor stretch.

Once the shoulder strap(s) 50A, 50B are attached to the person's flex leg FL, the person adjusts the length of the shoulder straps to move the knee toward their chest to flex the hip flexor on the flex leg. Specifically, movement of the knee toward the chest posteriorly tilts the pelvis and reduces the lumbar lordosis, thereby maximizing the stretch leg positioning for optimal lengthening of the hip flexors. As the knee is moved closer to the chest, the person will feel a mild static and passive stretch of the hip flexor on the stretch leg SL. The point at which the person feels this stretch varies from person to person. One person may feel the hip flexor on the stretch leg SL stretch when the knee of the flex leg FL is positioned such that the thigh of the flex leg FL is at an approximately 90° angle to the chest, however, a person may feel the stretch in the hip flexors of the stretch leg SL as the knee of the flex leg FL is moved before or after such a point. Using the shoulder straps 50A, 50B, the person moves the knee of the flex leg FL to their preferred location such that the person feels the hip flexors of the stretch leg SL are mildly stretched. Once set to the desired length, the shoulder straps 50A, 50B hold the person's knee in position during the stretch. As the person moves their knee on their flex leg FL, the stretch leg SL remains at rest in an extended position. As explained in more detail below, the different extended positions of the stretch leg SL can alter the point at which the person feels a stretch in the hip flexor and the severity of the hip flexor stretch felt.

Once the knee of the flex leg FL is moved such that the person feels the mild stretch in the hip flexors of the stretch leg SL, the person closes the valve of the pump 44 and operates the pump to inflate the inflatable bladders 16. The inflatable bladders 16 apply a posterior to anterior pressure to the hip area of the person in the supine position as the bladders inflate. In other words, as the inflatable bladders 16 are inflated by the pump 44, the bladders apply a lifting force at the hips generally directed vertically away from the upper surface 20 of the mat 12. This lifting force elevates the hip area, applying a capsular stretch of the anterior hip joint (generally the hip area) of the stretch leg SL, further stretching the hip flexor. After the inflatable bladders 16 are inflated, the person can hold the stretch for a period of time. In one use, the person deflates the inflatable bladders 16 after the stretch time is completed by operating the valve. In another use, the person operates the valve to slowly and gradually deflate the inflatable bladders 16 over the stretch time or for a part of the stretch time. The duration of the hip flexor stretch varies and may be anywhere between about 5 seconds and about 3 minutes. However, any duration of the stretch is within the scope of the present disclosure. In the preferred method of use, the inflatable bladders 16 are inflated to their maximum expansion and then allowed to fully deflate. This cycle is repeated two to three times, or as needed. After the stretching of the first hip flexor is completed, the person switches the knee strap 52 over to the opposite leg to stretch the hip flexor of the opposite leg. It will be understood that the leg which was previously the flex leg FL is now the stretch leg SL, and the leg that was previously the stretch leg is now the flex leg. Once the knee strap 52 is connected to the opposite leg the process, as described herein, is repeated to stretch the other hip flexor.

Figure 4:
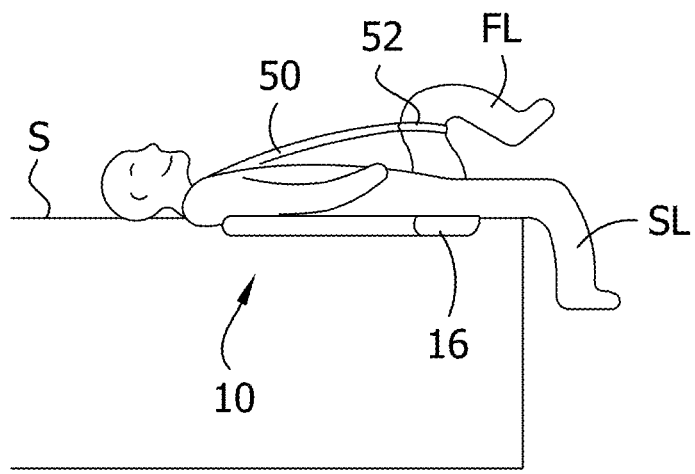
FIG. 4 is an illustration of the hip-stretching device in use during a medium-intensity stretch.
Figure 5:
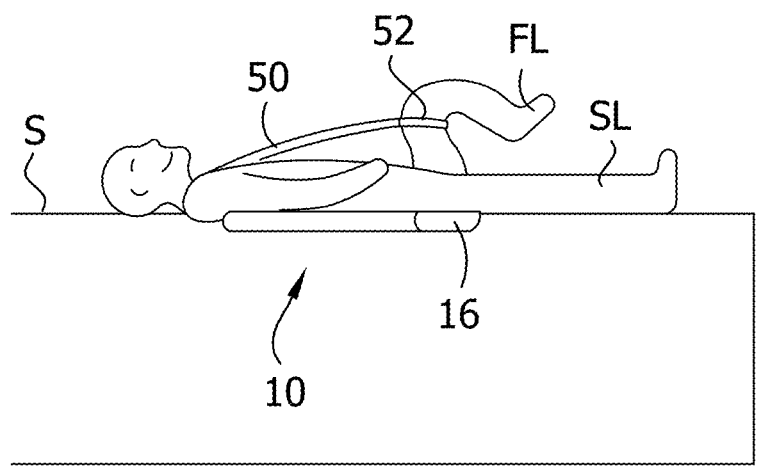
FIG. 5 is an illustration of the hip-stretching device in use during a low-intensity stretch.

Still referring to FIGS. 3-5, as mentioned above, the flex leg FL remains generally fixed in the flexed position while the stretch leg SL remains in the extended position to stretch the hip flexor. Various passive positions are possible depending on the person's preference and the intensity of the stretch desired. In the illustrated embodiments, three different extension positions of the stretch leg SL are shown. FIG. 3 shows the extension position of the stretch leg SL for a high-intensity stretch of the hip flexor. For the high intensity stretch, the hip-stretching device 10 is positioned on the support surface S such that when the person lays down in the supine position, the stretch leg SL is unsupported and completely hangs off an end of the support surface S. This position places the hip flexor in a hyper extended position. FIG. 4 shows the extension position of the stretch leg SL for a medium intensity stretch of the hip flexor. For the medium intensity stretch, the hip-stretching device 10 is positioned on the support surface S such that when the person is in the supine position, the upper part of the stretch leg SL is supported on the bed while the lower part of the stretch leg is unsupported and hangs off the end of the support surface S. FIG. 5 shows the extension position of the stretch leg SL for a low intensity stretch of the hip flexor. For the low intensity stretch, the hip-stretching device 10 is positioned on the support surface S such that when the person is in the supine position, the stretch leg SL is entirely supported by the support surface.

The positioning of the stretch leg SL in one of the disclosed extension positions pre-stresses or pre-stretches the hip flexor (more generally the hip area) before the device 10 further stretches the hip flexor by elevating the hip area using the inflatable bladders 16. The amount of pre-stretch the hip flexor experiences depends on the extension position of the stretch leg SL. In the extension position shown in FIG. 3 for the high intensity stretch, the stretch leg SL provides a maximum amount of pre-stretch in the hip flexor. In the extension position shown in FIG. 4 for the medium intensity stretch, the stretch leg SL provides a moderate amount of pre-stretch in the hip flexor. In the extension position shown in FIG. 5 for the low intensity stretch, the stretch leg SL provides the minimum amount of stretch in the hip flexor. The person selects the extension position of the stretch leg SL based upon the intensity of the hip flexor stretch desired and/or the position of the knee of the flex leg FL in which the person starts to feel the hip flexor stretch in the stretch leg. For example, a low intensity extension position of the stretch leg SL is appropriate if the person has relatively tight, inflexible hip flexors. However, if the person desires a more intense stretch, the person can change the extension position of the stretch leg SL to correspond to a greater intensity stretch (FIGS. 3 and 4) that pre-stretches the hip flexor a larger amount.

Figure 6:
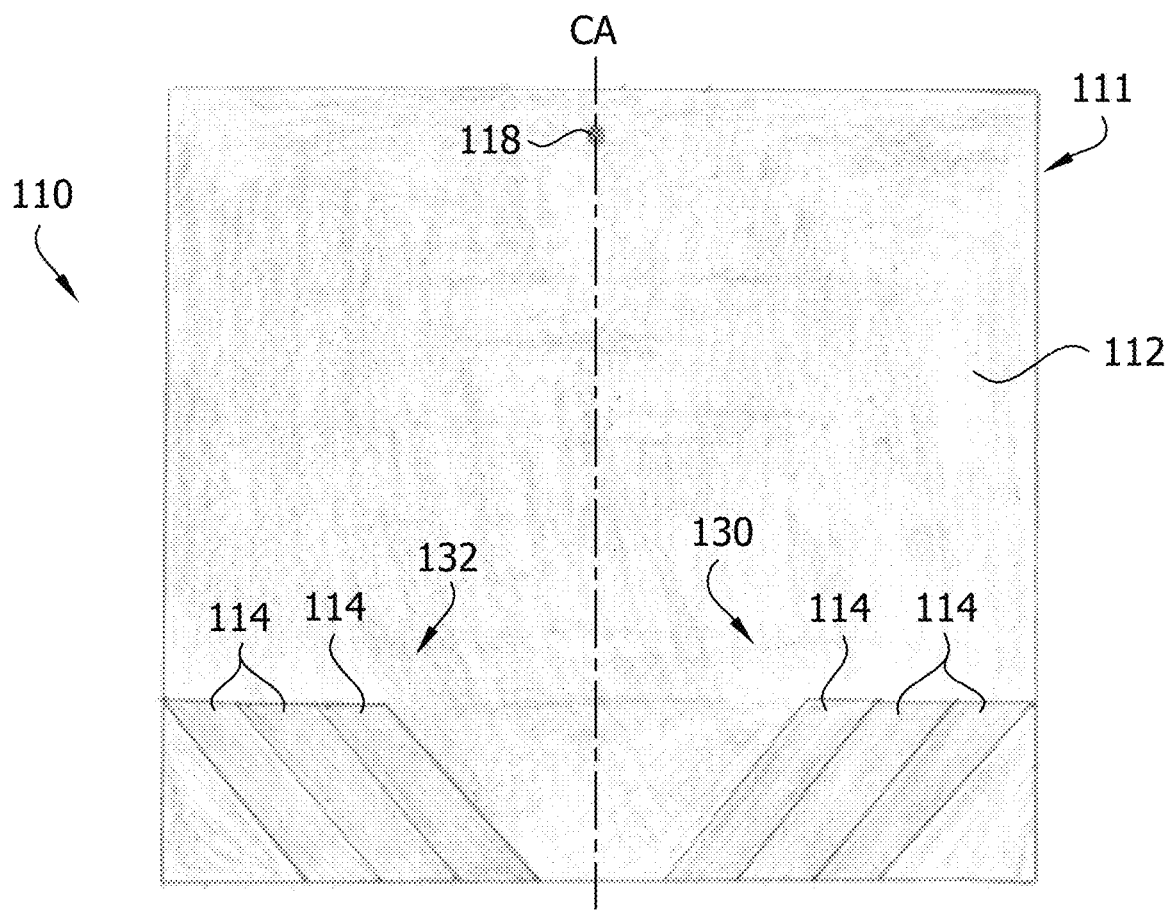
FIG. 6 is an illustration of a pad assembly of another embodiment.
Figure 7:
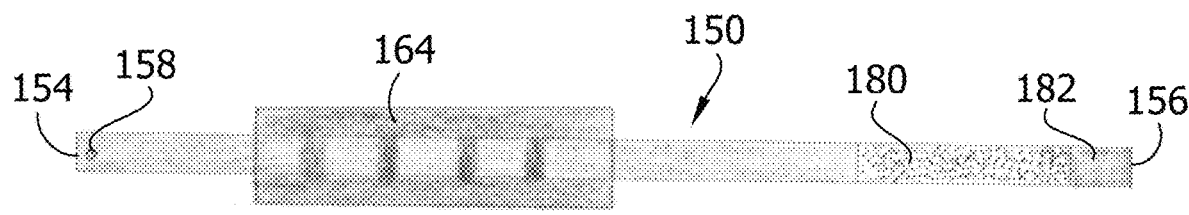
FIG. 7 is an illustration of a strap for use with the pad assembly of FIG. 6.

Referring to FIGS. 6 and 7, another embodiment of the hip-stretching device is generally indicated at 110. For ease of comprehension, where analogous parts are used, reference designators "100" units higher are employed. The hip-stretching device 110 is similar to the hip-stretching device 10 and operates in a similar way. Compared to the first embodiment, the hip-stretching device 110 has first and second sets of pockets 130 and 132, respectively, that are separated or spaced apart from one another such that pockets 114 of the first and second sets closest to the center of the mat 112 do not engage each other. Having first and second sets of pockets 130, 132 spaced apart allows the hip-stretching device 110 to conform to a person with a larger pelvic width. Moreover, the hip-stretching device 110 is configured to be used with only one shoulder strap 150. The mat 112 includes a single connector component 118 secured to the mat on the central axis CA to connect with a connector component 158 of the shoulder strap 150. The shoulder strap 150 is similar to shoulder straps 50A, 50B except that shoulder strap 150 includes Velcro, with hook and loops sections 180 and 182, respectively, at the distal end 156. The shoulder strap 150 can be releasably connected to the knee strap 52 by inserting the distal end 156 of the shoulder strap through the ring 74 of the knee strap and folding the shoulder strap back on itself to engage the hook and loops sections 180, 182 of the Velcro. In use, the person attaches the shoulder strap 150 to the mat 112 and extends the shoulder strap over the shoulder on the same side as the hip being stretched to attach the shoulder strap to the knee strap 152 on the flex leg (e.g. the shoulder strap extends across the person's body).

Figure 9:
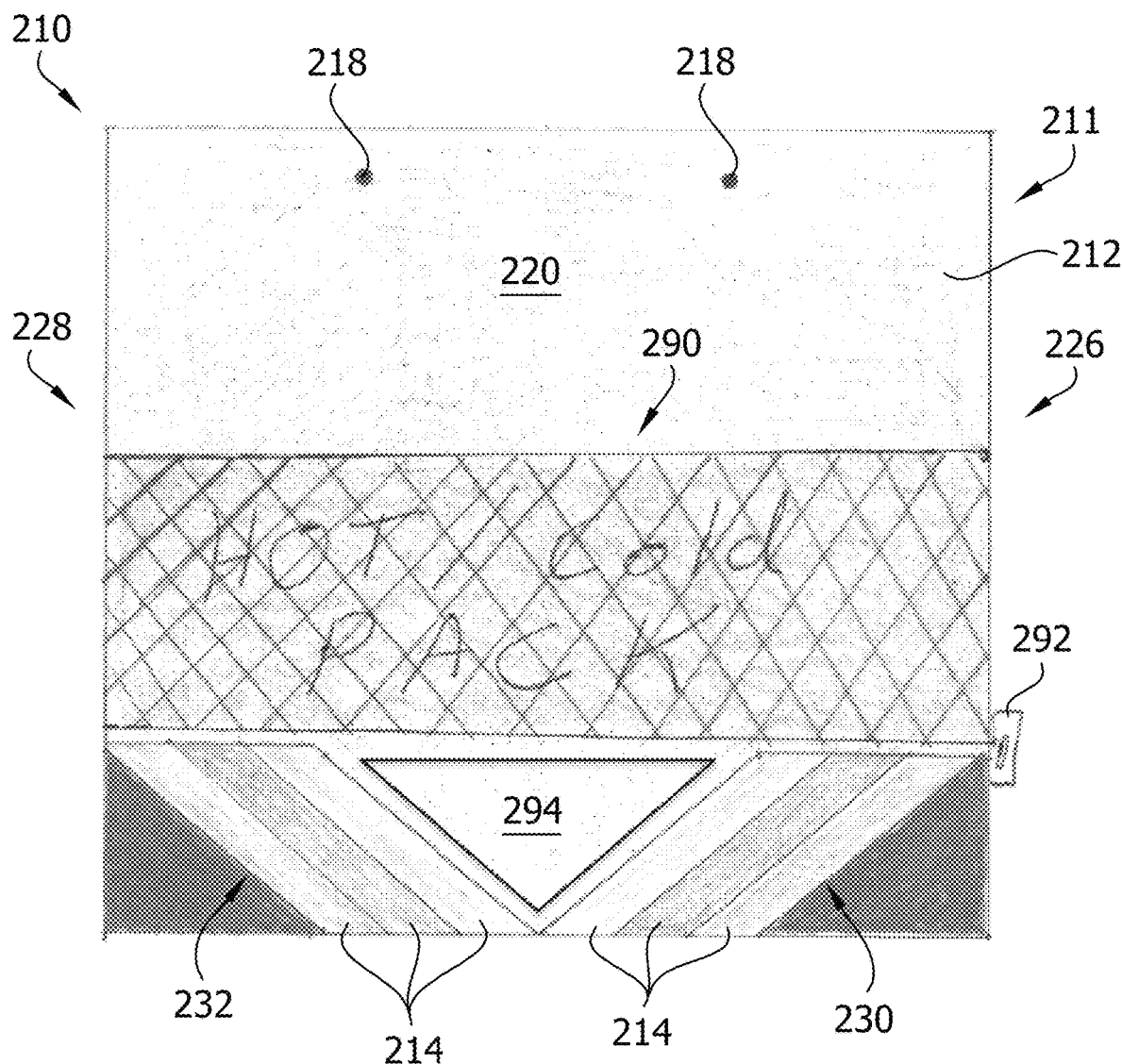
FIG. 9 is an illustration of a pad assembly of another embodiment.

Referring to FIG. 9, a hip-stretching device of another embodiment is generally indicated at 210. The hip-stretching device 210 is substantially similar to the hip-stretching device 10 of the first embodiment, therefore, where analogous parts are used, reference designators "200" units higher are employed. A pad assembly 211 includes a hot/cold pack pocket 290 and a vibrator 294. The hot/cold pack pocket 290 is configured to receive a heating or cooling device such as, but not limited to a heating pad, a cooling pad, or any other similar device, and hold the heating or cooling device near the hip flexors while the person is stretching. The hot/cold pack pocket 290 is located adjacent the pockets 214 on the upper surface 220. In the illustrated embodiment, the hot/cold pack pocket 290 extends across the mat 212 between the opposite first and second side edge margins 226, 228. This allows the hot/cold pack pocket 290 to receive a variety of different heating and/or cooling devices of different shapes and sizes. It is understood the hot/cold pack pocket 290 may have other configurations within the scope of the present disclosure. The hot/cold pack pocket 290 has an opening (not shown) allowing the heating or cooling device to be inserted into and removed from the pocket. If the user desires to heat or cool the hip flexors during the stretch, the user can insert the heating or cooling device into the hot/cold pack pocket 290 before lying on the mat 212 in a supine position. The vibrator 294 is configured to vibrate the hip flexors and lower portion of the user's back as the person stretches. The user can selectively operate the switch 292 to massage the hip flexors and adjacent area as desired during the stretch. For example, the person can operate the vibrator 294 during the entire duration of the stretch, intermittently during the stretch or any other suitable time. In the illustrated embodiment, the vibrator 294 is positioned between the first and second sets of pockets 230, 232. It is understood the vibrator 294 can have other configuration within the scope of the present disclosure. The vibrator 294 may be connected to a power supply (not shown), such as an outlet or battery pack, and selectively turned on and off by a switch 292. Both the hot/cold pack pocket 290 and the vibrator 294 can be formed integrally with the mat 212 or formed separately and suitably attached and/or positioned on the mat. It is understood the hot/cold pack pocket 290 and vibrator 294 are possible additional features to the pad assembly 11 of hip-stretching device 10 and the pad assembly 111 of hip-stretching device 110, and the hip-stretching devices may include one, both, or neither of them.

In view of the above, it will be seen that the several features of the invention are achieved and other advantageous results obtained.

Through the inclusion of multiple pockets 14, 114, 214, the hip-stretching device 10, 110, 210 is adjustable to the pelvic width of each individual user. Moreover, the hip-stretching device 10, 110, 210 is able to hold the person's knee in position for stretching the hip flexor of the opposite leg for a period of time when the person is in the supine position. In addition, by inflating the inflatable bladders 16, 116 positioned under the hip flexor, the hip-stretching device 10, 110, 210 is able to lift or elevate the hip area of a person to further stretch the hip flexor.

Having described the invention in detail, it will be apparent that modifications and variations are possible without departing from the scope of the invention defined in the appended claims. For example, where specific dimensions are given, it will be understood that they are exemplary only and other dimensions are possible.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above products without departing from the scope of the invention, it is intended that all matter contained in the above description and shown in the accompanying drawings shall be interpreted as illustrative and not in a limiting sense.

What is claimed is:

1. A hip-stretching device comprising:
   a mat having an upper surface and configured for placement on a support surface to support a back of a subject lying in a supine position on the upper surface of the mat; and
   first and second pockets associated with the mat, each of the first and second pockets having an opening configured to removably receive an inflatable bladder for selectively placing the inflatable bladder in one of the first and second pockets, the first and second pockets each positioning an inflatable bladder received therein under a hip area of the subject when the subject is lying in the supine position on the upper surface of the mat such that inflation of the inflatable bladder imparts a force to the hip area of the subject to elevate the hip area providing a hip flexor stretch to the subject.

2. The hip-stretching device of claim 1, wherein the mat has a top edge margin, a bottom edge margin, and a central axis extending between the top and bottom edge margins, the first and second pockets being positioned on opposite sides of the central axis.

3. The hip-stretching device of claim 2, wherein each of the first and second pockets has a closed end opposite the opening, the first pocket defining a first longitudinal axis extending between the opening and closed end of the first pocket, the second pocket defining a second longitudinal axis extending between the opening and closed end of the second pocket, the first longitudinal axis being non-parallel with the second longitudinal axis.

4. The hip-stretching device of claim 3, further comprising third and fourth pockets associated with the mat, each of the third and fourth pockets having an opening configured to removably receive an inflatable bladder.

5. The hip-stretching device of claim 4, wherein the third pocket is immediately adjacent to the first pocket and the fourth pocket is immediately adjacent to the second pocket.

6. The hip-stretching device of claim 5, wherein each of the third and fourth pockets have a closed end opposite the opening, the third pocket defining a third longitudinal axis extending between the opening and closed end of the third pocket, the fourth pocket defining a fourth longitudinal axis extending between the opening and closed end of the fourth pocket, the third longitudinal axis being generally parallel to the first longitudinal axis and the fourth longitudinal axis being generally parallel to the second longitudinal axis.

7. The hip-stretching device of claim 6, wherein the third pocket has a centerpoint and the fourth pocket has a centerpoint, the distance between the centerpoint of the third pocket and the centerpoint of the fourth pocket being between about 9 and about 12 inches.

8. The hip-stretching device of claim 6, further comprising fifth and sixth pockets associated with the mat, each of the fifth and sixth pockets having an opening configured for removably receiving an inflatable bladder and a closed end opposite the opening, the fifth pocket being positioned immediately adjacent to the third pocket, the sixth pocket being positioned immediately adjacent to the fourth pocket, the fifth pocket defining a fifth longitudinal axis extending between the opening and closed end of the fifth pocket, the sixth pocket defining a sixth longitudinal axis extending between the opening and closed end of the sixth pocket, the fifth longitudinal axis being generally parallel to the first and third longitudinal axis and the sixth longitudinal axis being generally parallel to the second and fourth longitudinal axis.

9. The hip-stretching device of claim 8, further comprising first and second inflatable bladders, wherein the first inflatable bladder is configured for receipt in one of the first, third and fifth pockets and the second inflatable bladder is configured for receipt in one of the second, fourth and sixth pockets.

10. The hip-stretching device of claim 9, further comprising a pump fluidly connected to the first and second inflatable bladders.

11. The hip-stretching device of claim 10, further comprising a valve connected to the pump, the valve configured to allow air to escape the first and second inflatable bladders.

12. The hip-stretching device of claim 1, wherein the mat has a top edge margin, a bottom edge margin, and a central axis extending between the top and bottom edge margins, the first and second pockets being positioned on the same side of the central axis.

13. The hip-stretching device of claim 12, wherein each of the first and second pockets has a closed end opposite the opening, the first pocket defining a first longitudinal axis extending between the opening and closed end of the first pocket, the second pocket defining a second longitudinal axis extending between the opening and closed end of the second pocket, the first longitudinal axis being parallel with the second longitudinal axis.

14. The hip-stretching device of claim 1, wherein the mat has a top edge margin, a bottom edge margin, and a central axis extending between the top and bottom edge margins, the first and second pockets each having a longitudinal axis extending at a non-parallel angle to the central axis, and wherein the central axis and the longitudinal axis of the first and second pockets extend in a common plane.

15. The hip-stretching device of claim 14, wherein the longitudinal axis of each of the first and second pockets extends from the central axis at an angle between about 30 and about 50 degrees.

16. The hip-stretching device of claim 1, further comprising a knee strap and a first shoulder strap, the knee strap configured to be secured proximate to a knee of the subject, the first shoulder strap having a first end and a second end, the mat including a connector so that the first end of the first shoulder strap can be secured directly to the mat, the second end of the first shoulder strap configured to releasably attach to the knee strap.

17. The hip-stretching device of claim 16, further comprising a second shoulder strap, the second shoulder strap having a first end and a second end, the mat including a second connector so that the first end of the second shoulder strap can be secured directly to the mat, the second end of the second shoulder strap configured to releasably attach to the knee strap.

18. The hip-stretching device of claim 17, wherein the first and second shoulder straps each have a length extending between the first and second ends, the lengths of the first and second shoulder straps being adjustable.

19. A method of stretching a hip flexor of a person, the method comprising:
providing a hip-stretching device including a mat, at least two pockets associated with the mat, and an inflatable bladder configured to be removably inserted into one of the at least two pockets;
inserting the inflatable bladder into one of the at least two pockets;
laying the mat on a support surface and positioning the mat underneath the person such that the inflatable bladder inserted into one of the at least two pockets is disposed beneath a hip flexor of the person; and
inflating the inflatable bladder to stretch the hip flexor.

20. The method of claim 19, wherein the hip-stretching device further includes a first set of pockets positioned for being disposed beneath a left hip flexor of the person when the mat is positioned underneath the person and a second set of pockets positioned for being disposed beneath a right hip flexor of the person when the mat is positioned underneath the person, the method further comprising:
inserting an inflatable bladder into a pocket of the first set of pockets;
inflating the inflatable bladder inserted into the pocket of the first set of pockets to stretch the left hip flexor of the person;
inserting an inflatable bladder into a pocket of the second set of pockets; and
inflating the inflatable bladder inserted into the pocket of the second set of pockets to stretch the right hip flexor of the person.

* * * * *